US007629659B2

United States Patent
Jacobsen et al.

(10) Patent No.: US 7,629,659 B2
(45) Date of Patent: Dec. 8, 2009

(54) MINIATURIZED IMAGING DEVICE WITH INTEGRATED CIRCUIT CONNECTOR SYSTEM

(75) Inventors: Stephen C. Jacobsen, Salt Lake City, UT (US); David T. Markus, Salt Lake City, UT (US); David P. Marceau, Salt Lake City, UT (US); Ralph W. Pensel, Sandy, UT (US)

(73) Assignee: Sterling LC, Salt Lake City, UT (US)

( * ) Notice: Subject to any disclaimer, the term of this patent is extended or adjusted under 35 U.S.C. 154(b) by 0 days.

(21) Appl. No.: 12/079,741

(22) Filed: Mar. 27, 2008

(65) Prior Publication Data

US 2008/0185672 A1  Aug. 7, 2008

Related U.S. Application Data

(62) Division of application No. 10/391,513, filed on Mar. 17, 2003.

(60) Provisional application No. 60/431,261, filed on Dec. 6, 2002, provisional application No. 60/365,561, filed on Mar. 18, 2002, provisional application No. 60/365,692, filed on Mar. 18, 2002.

(51) Int. Cl.
  *H01L 31/048* (2006.01)
(52) U.S. Cl. ............... 257/432; 257/433; 257/E31.127
(58) Field of Classification Search ............... 257/432, 257/433, E31.127
  See application file for complete search history.

(56) References Cited

U.S. PATENT DOCUMENTS

| 3,971,065 A | 7/1976 | Bayer |
| 4,283,115 A | 8/1981 | Fraissl |
| 4,487,206 A | 12/1984 | Aagard |
| 4,515,444 A | 5/1985 | Prescott et al. |

(Continued)

FOREIGN PATENT DOCUMENTS

EP    0482997 A1 * 10/1991

(Continued)

OTHER PUBLICATIONS

Nguyen, Clark, "Communications Applications of Microelectromechanical Systems," Proceedings, Sensors Expo, May 19-21, 1998, San Jose, CA. pp. 447-455.

(Continued)

*Primary Examiner*—Allan R. Wilson
(74) *Attorney, Agent, or Firm*—Thorpe North & Western LLP

(57) ABSTRACT

A miniaturized imaging device and method of viewing small luminal cavities are described. The imaging device can be used as part of a catheter, and can include a lens, an SSID including an imaging array optically coupled to the lens; an umbilical including a conductive line; and an adaptor configured to support the lens and provide electrical communication between the SSID and conductive line. Alternatively, the adaptor can be a rigid adaptor configured to provide electrical communication between the SSID and the conductive line through a conductive path. The conductive path can be configured along multiple contiguous surfaces of the adaptor such that the SSID is electrically coupled to the conductive path at a first surface, and the conductive line is electrically coupled to the conductive path at a second surface.

19 Claims, 13 Drawing Sheets

U.S. PATENT DOCUMENTS

| | | | |
|---|---|---|---|
| 4,573,450 A | 3/1986 | Arakawa |
| 4,604,992 A | 8/1986 | Sato |
| 4,620,534 A | 11/1986 | Zartman |
| 4,622,954 A | 11/1986 | Arakawa et al. |
| 4,646,724 A | 3/1987 | Sato et al. |
| 4,706,118 A | 11/1987 | Kato et al. |
| 4,723,843 A | 2/1988 | Zobel |
| 4,745,470 A | 5/1988 | Yabe et al. |
| 4,745,471 A | 5/1988 | Takamura et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,926,257 A | 5/1990 | Miyazaki |
| 4,932,394 A | 6/1990 | Nanaumi |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,040,069 A | 8/1991 | Matsumoto et al. |
| 5,061,036 A | 10/1991 | Gordon |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,130,804 A | 7/1992 | Tamura et al. |
| 5,166,656 A | 11/1992 | Badehi et al. |
| 5,191,203 A | 3/1993 | McKinley |
| 5,198,894 A | 3/1993 | Hicks |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,291,010 A | 3/1994 | Tsuji |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,455,455 A | 10/1995 | Badehi |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,531,664 A | 7/1996 | Adachi et al. |
| 5,547,906 A | 8/1996 | Badehi |
| 5,594,497 A | 1/1997 | Ahern et al. |
| 5,603,687 A | 2/1997 | Hori et al. |
| 5,630,788 A | 5/1997 | Forkner et al. |
| 5,647,368 A | 7/1997 | Zeng et al. |
| 5,673,083 A | 9/1997 | Izumi et al. |
| 5,693,043 A | 12/1997 | Kittrell et al. |
| 5,716,323 A | 2/1998 | Lee |
| 5,716,759 A | 2/1998 | Badehi |
| 5,722,403 A | 3/1998 | McGee et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,792,984 A | 8/1998 | Bloom |
| 5,800,341 A | 9/1998 | McKenna et al. |
| 5,808,665 A | 9/1998 | Green |
| 5,818,644 A | 10/1998 | Noda |
| 5,827,172 A | 10/1998 | Takahashi et al. |
| 5,840,017 A | 11/1998 | Furusawa et al. |
| 5,848,969 A | 12/1998 | Panescu et al. |
| 5,865,729 A | 2/1999 | Meehan et al. |
| 5,873,816 A | 2/1999 | Kagawa et al. |
| 5,904,651 A | 5/1999 | Swanson et al. |
| 5,908,445 A | 6/1999 | Whayne et al. |
| 5,913,817 A | 6/1999 | Lee |
| 5,929,900 A | 7/1999 | Yamanaka et al. |
| 5,940,126 A | 8/1999 | Kimura |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,999,327 A | 12/1999 | Nagaoka |
| 6,008,123 A | 12/1999 | Kook et al. |
| 6,022,758 A | 2/2000 | Badehi |
| 6,040,235 A | 3/2000 | Badehi |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,142,930 A | 11/2000 | Ito et al. |
| 6,161,035 A | 12/2000 | Furusawa |
| 6,184,923 B1 | 2/2001 | Miyazaki |
| 6,261,226 B1 | 7/2001 | McKenna et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,366,726 B1 | 4/2002 | Wach et al. |
| 6,384,397 B1 | 5/2002 | Takiar et al. |
| 6,396,116 B1 | 5/2002 | Kelly et al. |
| 6,485,413 B1 | 11/2002 | Boppart et al. |
| 6,533,722 B2 | 3/2003 | Nakashima |
| 6,595,913 B2 | 7/2003 | Takahashi |
| 6,624,138 B1 | 9/2003 | Tu et al. |
| 6,643,071 B2 | 11/2003 | Schnitzer |
| 6,826,422 B1 | 11/2004 | Modell et al. |
| 6,827,683 B2 | 12/2004 | Otawara |
| 6,834,158 B1 | 12/2004 | Templeton |
| 6,898,458 B2 | 5/2005 | Zeng et al. |
| 6,937,268 B2 | 8/2005 | Ogawa |
| 6,982,740 B2 | 1/2006 | Adair et al. |
| 7,030,904 B2 | 4/2006 | Adair et al. |
| 7,091,500 B2 | 8/2006 | Schnitzer |
| 7,153,299 B1 | 12/2006 | Tu et al. |
| 7,166,537 B2 | 1/2007 | Jacobsen et al. |
| 7,221,388 B2 | 5/2007 | Sudo et al. |
| 2001/0007051 A1 | 7/2001 | Nakashima |
| 2001/0007511 A1 | 7/2001 | Minami et al. |
| 2001/0024848 A1 | 9/2001 | Nakamura |
| 2001/0049509 A1 | 12/2001 | Sekine et al. |
| 2002/0007110 A1 | 1/2002 | Irion |
| 2002/0080248 A1 | 6/2002 | Adair et al. |
| 2002/0111534 A1 | 8/2002 | Suzuki et al. |
| 2003/0071342 A1 | 4/2003 | Honda et al. |
| 2003/0220574 A1 | 11/2003 | Markus et al. |
| 2003/0222325 A1 | 12/2003 | Jacobsen et al. |
| 2004/0017961 A1 | 1/2004 | Petersen et al. |

| | | |
|---|---|---|
| 2004/0225222 A1 | 11/2004 | Zeng et al. |
| 2005/0154277 A1 | 7/2005 | Tang et al. |
| 2005/0267340 A1 | 12/2005 | Ishihara et al. |
| 2006/0146172 A1 | 7/2006 | Jacobsen et al. |

FOREIGN PATENT DOCUMENTS

| | | |
|---|---|---|
| EP | 0639043 | 2/1995 |
| EP | 0681809 | 11/1995 |
| EP | 1104182 | 5/2001 |
| JP | 63-155115 | 6/1988 |
| JP | 5-049602 | 3/1993 |
| JP | 58-046924 | 3/1993 |
| WO | WO98/38907 | 9/1998 |
| WO | WO99/40624 | 8/1999 |
| WO | WO00/54033 | 9/2000 |

OTHER PUBLICATIONS

Fujimoto, JG et al., "High resolution in vivo intra-arterial imaging with optical coherence tomography," Heart, 1999, vol. 82, pp. 128-133.

Boppart, S.A. et al., "Forward-imaging instruments for optical coherence tomography." Optics Letters, Nov. 1, 1997, vol. 22, No. 21, pp. 1618-1620.

Tearney, G.J. et al., "Scanning single-mode fiber optic catheter-endoscope for otpical coherence tomography," Optics Letters, Apr. 1, 1996, vol. 21, No. 7, pp. 543-545.

Boppart, S.A. et al., "Optical imaging technology in minimally invasive surgery," Surg. Endosc., 1999, vol. 13, pp. 718-722.

Zeis, Michael et al., "Color Business Report," ISSN 1055-3339. Jul. 2002, p. 5.

Microcam, MINAST Project 5.04, Nov. 11, 1999, http://www.imt.unine.ch/ESPLAB/www/projects/Microcam/, pp. 1-16.

Literature from GRIN TECH, "In vivo medical confocal imaging and optical coherence tomography," www.grintech.de, Revision Jun. 2001, pp. 1-3.

Jacobsen, Stephen C., U.S. Appl. No. 12/152,730, filed May 16, 2008.

Jacobsen, Stephen C., U.S. Appl. No. 10/391,513, filed Mar. 17, 2003.

Jacobsen, Stephen C., U.S. Appl. No. 11/292,902, filed Dec. 1, 2005.

Jacobsen, Stephen C., U.S. Appl. No. 12/008,486, filed Jan. 11, 2008.

Jacobsen, Stephen C., U.S. Appl. No. 11/810,702, filed Jun. 5, 2007.

* cited by examiner

MINIATURIZED IMAGING DEVICE WITH INTEGRATED CIRCUIT CONNECTOR SYSTEM

This present application is a division of U.S. application Ser. No. 10/391,513 filed in the U.S. Patent Office on Mar. 17, 2003, which claims priority to U.S. Provisional Application No. 60/365,561 filed in the U.S. Patent Office on Mar. 18, 2002, U.S. Provisional Application No. 60/365,692 filed in the U.S. Patent Office on Mar. 18, 2002 and U.S. Provisional Application No. 60/431,261 filed in the U.S. Patent Office on Dec. 6, 2002, each of which are incorporated herein in their entirety.

FIELD OF THE INVENTION

The invention relates generally to solid state imaging devices (SSIDs). More specifically, the invention relates to miniaturized imaging devices that are particularly suited to viewing beyond small openings and traversing small-diameter areas. These devices can be used for catheter-borne medical imaging within the anatomy of a patient, and are useful for other applications.

BACKGROUND OF THE INVENTION

Small imaging devices that take advantage of advances in integrated circuit imaging technologies are known. Such small imaging devices can be particularly useful in medical diagnostic and treatment applications. Portions of human anatomy previously viewable only by a surgical procedure can be viewed now by a minimally invasive catheterization, provided an imaging device can be made that is small enough to view the target anatomy.

Other uses for very small imaging devices are recognized. For example, such devices can be used and are desirable for surveillance applications, for monitoring of conditions and functions within devices, and for size- and weight-critical imaging needs as are present in aerospace applications, to name a few.

While the present invention has applications in these aforementioned fields and others, the medical imaging application can be used to favorably illustrate unique advantages of the invention. The desirability of providing imaging at sites within the anatomy of living creatures, especially humans, distal of a small orifice or luminal space has long been recognized. A wide variety of types and sub-types of endoscopes have been developed for this purpose.

One advance in imaging technology which has been significant is in the area of SSIDs. Such devices, including the charge-injection device (CID), the charge-coupled device (CCD), and the complementary metal oxide semiconductor (CMOS) device, provide good alternatives to the use of bundled fiber optics, as well as to conventional miniaturized imaging devices used in endoscope applications. However, when considering a design of a catheter-borne imaging device, consideration should be given to the ability of a distal tip of the catheter to flex and bend, without breaking or becoming damaged. This is necessary to accommodate limitations of anatomy to minimize trauma, and to enable steering of the distal tip to a desired location.

Accordingly, there is a desire to manufacture smaller devices that are steerable and provide good image quality for the size.

SUMMARY OF THE INVENTION

It has been recognized that by looking outside conventional devices and techniques, that facilitation of further miniaturization of an imaging device employing SSIDs at a distal end of a catheter or other flexible umbilical can be accomplished. The invention accordingly provides a miniaturized imaging device, comprising a lens, an SSID, an umbilical, and an adaptor. The lens can be a GRIN lens, or another type of lens, including a wide angle lens or prism lens. The SSID can include an imaging array optically coupled to the lens. The umbilical can include a conductive line, such as a plurality of conductive wires to provide power, ground, clock signal, and output signal. In another embodiment, the conductive line can include at least two conductive wires that are electrically isolated from one another. The adaptor can be configured to support the lens and provide electrical communication between the SSID and conductive line.

In an alternative embodiment, a miniaturized imaging device can comprise a lens, an SSID including an imaging array optically coupled to the lens, an umbilical including a conductive line, and a rigid adaptor. The rigid adaptor can be configured to provide electrical communication between the SSID and the conductive line through a conductive path. The conductive path can be configured along multiple contiguous surfaces of the adaptor such that the SSID is electrically coupled to the conductive path at a first surface, and the conductive line is electrically coupled to the conductive path at a non-coplanar second surface.

With respect to both of the above embodiments, in one embodiment, the adaptor can be configured to have a side surface and an adjacent bottom surface, wherein a conductive strip is present that has electrically continuous properties from the side surface to the bottom surface. The conductive line of the umbilical, such as electrical wires, can be configured to electrically contact one or more conductive strip at the side surface of the adaptor. Further, the SSID can electrically contact the conductive strip(s) at the bottom surface of the adaptor. Thus, the conductive line can be placed in electrical communication with the SSID through the adaptor. Other configurations are also available, as will be described by example hereinafter. In one embodiment, the adaptor can be configured such that multiple separate electrical signals, e.g., four, can pass therethrough at the same time without the signals substantially interfering with one another. As the microcamera described herein can be very small, the adaptor can be smaller than 500 microns in length, width, and height, respectively.

The SSID typically includes an imaging array, and can further include conductive pads electrically coupled to the imaging array. The conductive pads can provide electrical communication between the SSID and the conductive line through the adaptor. The SSID can be one of many known SSIDs, including a CCD, a CID, or a CMOS imaging device.

The optical coupling of the lens and the imaging array of the SSID can be direct, or can be through an optical intermediate device, such as a color filter insert, a fiber optic, a prism, or a wide angle lens, for example. To exemplify this principle, a color filter insert is described herein in detail. In one embodiment, a color filter insert can be used for producing multiple colors from a monochromatic camera image. An example of such a color filter insert includes a filter configured in a Bayer filter pattern.

A utility guide can also optionally be present. Such a utility guide can be configured for carrying utilities to the SSID, adaptor, or lens. Typically, a utility that can be present includes a light source carried by the SSID, the adaptor, and/or the utility guide. Alternative or additional utilities that can be present include electrical wires, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators. These utilities can be carried to a distal tip of the device via the umbilical.

In an alternative embodiment, a method of operating a microcamera, such as for viewing within or beyond a small luminal opening, can comprise the steps of (a) optically coupling a lens to an imaging array of an SSID, wherein the SSID is electrically coupled to a rigid adaptor; (b) defining a plurality of conductive paths, wherein at least one of the conductive paths is configured along multiple non-coplanar surfaces of the adaptor; (c) powering the SSID through a first of the conductive paths; and (d) receiving signal from the SSID through a second of the conductive paths. In one embodiment, the adaptor can be configured to support the lens as well. The method can further comprise the step of illuminating an area around the lens, such that light or photon energy can be received by an imaging array of the SSID.

The step of optically coupling the lens to the SSID can be by directly attaching the lens to an imaging array of the SSID, such as by an optically clear epoxy substance. Alternatively, the step of optically coupling the lens to the SSID can be by interposing an intermediate optical device between the lens and an imaging array of the SSID.

Though multiple conductive paths can include as few as two conductive paths, in one embodiment, the step of defining a plurality of conductive paths includes defining at least four conductive paths. In this configuration, ground can be provided to the SSID through a third conductive path, and control can be provided to the SSID through a fourth conductive path.

In another embodiment, a method of making an adaptor or connector block in accordance with an embodiment of the present invention includes the steps of (a) applying a conductive material layer to an adaptor substrate; (b) applying a photoresist material layer to the conductive material layer; (c) developing a portion of the photoresist material layer, such that a first portion of the conductive material layer is exposed, and a second portion of the conductive material layer is protected; and (d) removing the first portion of the conductive material from the adaptor substrate. Other steps can include the preliminary steps of applying a removable layer to a working substrate, followed by applying the adaptor substrate to the removable layer. Additionally, a step of removing the adaptor substrate from the removable layer after the first portion of the conductive material is removed from the adaptor substrate can also be carried out.

The step of developing a portion of the photoresist material can be by applying heat from beneath the working substrate, and/or applying UV light to a portion of the photoresist material that protects the first portion of the conductive material. This selective application of UV light can be accomplished by using a photomask. Typically, the photoresist material is completely removed after the first portion of the conductive material is removed from the adaptor substrate. If the adaptor is used for embodiments wherein a lens is supported by the adaptor, the step of drilling a hole through the adaptor substrate to configure the adaptor to also support a lens can be carried out. With respect to these adaptors, typically, the adaptor is less than 500 microns in length, width, and height, respectively.

Additional features and advantages of the invention will be apparent from the detailed description which follows, taken in conjunction with the accompanying drawings, which together illustrate, by way of example, features of the invention.

DETAILED DESCRIPTION OF THE PREFERRED EMBODIMENT(S)

Figure 1:
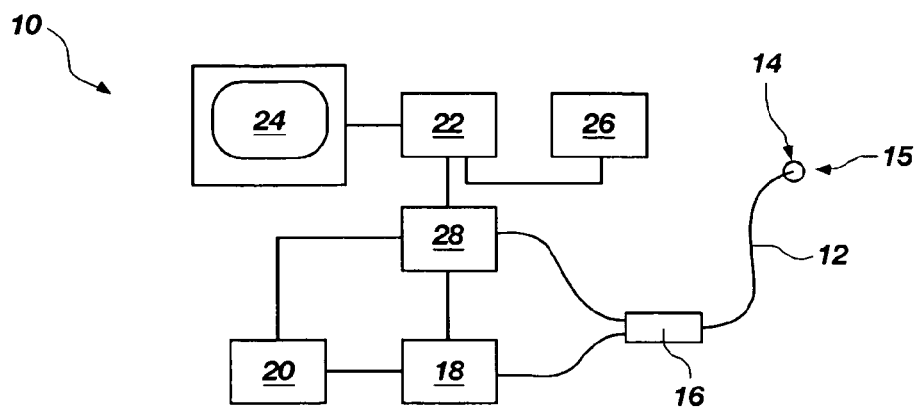
FIG. 1 is a schematic illustration of an exemplary medical imaging system in accordance with principles of the invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," or "SSID chip" in the exemplary embodiments generally comprises a substrate carrying an imaging array or pixel array for gathering image data, and can further comprise conductive pads electrically coupled to the imaging array, which facilitates electrical communication therebetween. In one embodiment, the SSID can comprise a silicon or silicon-like substrate or amorphous silicon thin film transistors (TFT) having features typically manufactured therein. Features can include the imaging array, the conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s), for providing power, ground, clock signal, and output signal with respect to the SSID, though not all of these are strictly required. For example, ground can be provide by another means than through an umbilical wire, e.g., to a camera housing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the affects of a more traditionally shaped lens. Though a GRIN lens is often used to exemplify an embodiment of the invention, the use of such a lens is not required. Other lenses can also be used as are known by those skilled in the art.

"Adaptor" "connector block," or "integrated circuit connector system" refers to a rigid device that can provide a solid electrical connection between a conductive line of an umbilical and conductive pads of an SSID. In one embodiment, the adaptor or connector block can function to support the lens as well.

With these definitions in mind, reference will now be made to the accompanying drawings, which illustrate, by way of example, embodiments of the invention.

Figure 2:
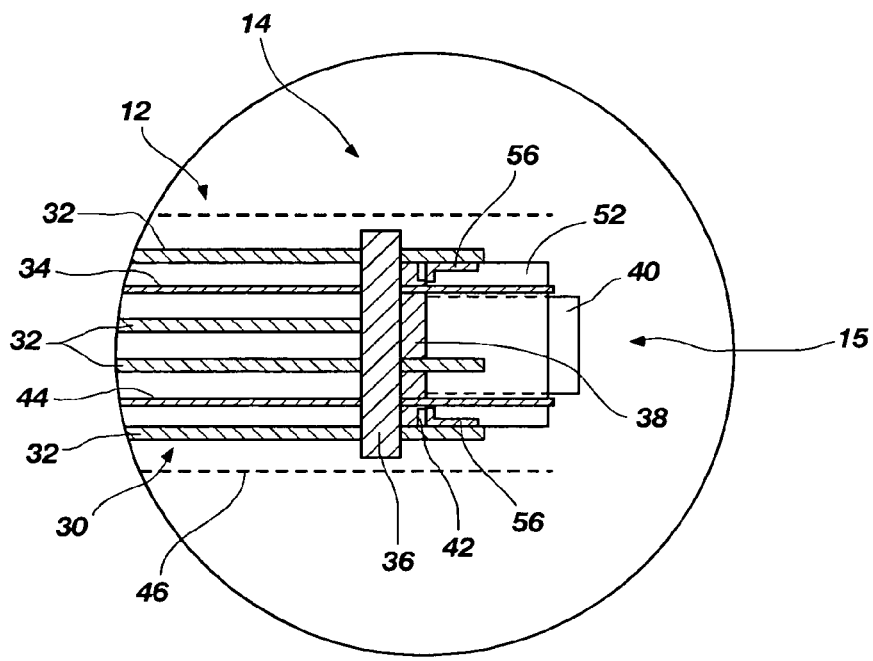
FIG. 2 is a side view of an exemplary embodiment of the present invention, which is an enlarged view of device 14 of FIG. 1.

With reference to FIGS. 1 and 2, the invention is embodied in a medical imaging system 10, including a catheter 12 having an imaging capability by means of an imaging device, shown generally at 14, at a distal tip 15 of the catheter. The system further includes a fitting 16 enabling an imaging fluid, such as a clear saline solution, to be dispensed to the distal tip portion of the catheter from a reservoir 18 to displace body fluids as needed to provide a clearer image. A pump 20 is provided, and is manually actuated by a medical practitioner performing a medical imaging procedure, or can be automated and electronically controlled so as to dispense fluid on demand according to control signals from the practitioner, sensors, or according to software commands.

A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical 30, including conductive wires 32, a fluid dispenser 34, and a light source 44, through the catheter 12. The interface can also be configured to control the pump 20 based on control signals from the processor or a medical practitioner performing an imaging procedure.

With more specific reference to FIG. 2, the imaging device 14 at the distal tip 15 can include a utility guide 36 for supporting or carrying the umbilical 30, which can include electrical wires 32, a fluid dispenser 34, and a light source 44. Other components that can be carried by the utility guide can include, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators. The utility guide can also carry an SSID or solid state imaging device 38 that includes an imaging array (not shown) and conductive pads 42 for coupling the electrical wires to the SSID.

In the embodiment shown, the SSID 38 is electrically bonded to electrical or conductive wires 32 through an adaptor 52. The adaptor provides the dual function of supporting a lens 40 (which in this embodiment, is a GRIN lens), and innervating the SSID via the umbilical. More specifically, power, signal, and control commands are carried to and from the SSID through metal traces or conductive strips 56 that extend from a side surface to a bottom surface of the adaptor.

The light source 44 shown is a fiber optic carried by the utility guide 36. However, other light sources can be used, such as those carried by the SSID 38 or adaptor 52. For example, the SSID or adaptor can include light-emitting diodes (LEDs) configured to illuminate the area immediately adjacent the distal tip portion.

The lens 40 can be a GRIN lens that is substantially cylindrical in shape, which is optically coupled to the imaging array of the SSID 38. In one embodiment, the GRIN lens can have a first flat end for receiving light, a second flat end for passing the light to the imaging array, and an outer curved surface surrounded by an opaque coating or sleeve member to prevent unwanted light from entering the GRIN lens. The GRIN lens can be optically coupled to the imaging array by direct contact between the second flat end and the imaging array of the SSID. Such direct contact can include an optically transparent or translucent bonding material at the interface between the second flat end and the imaging array. Alternatively, the GRIN lens can be optically coupled to the imaging array of the SSID through an intermediate optical device, such as a fiber optic or a color filter, or any shape optical lens such as a prism or wide angle lens. Though a GRIN lens is shown in this embodiment, other lenses that can be optically coupled to an SSID 38 can be used, as will be exemplified hereinafter.

The catheter 12 can be configured to be bendable and flexible so as to be steerable within a patient's anatomy and to minimize trauma. For example, the catheter can comprise a micromachined tube 46 at the distal tip portion, and cut-out portions (not shown) can allow for increased flexibility of the tube, and also allow for outflow of an imaging fluid to displace body fluids in the immediate area of the distal tip portion for more clear imaging. Such a micromachined tube can also allow bending to facilitate guiding the catheter to a desired location by selection of desired pathways as the catheter is advanced.

The catheter 12 can comprise an internal tensionable wire (not shown) adjacent one side of the distal tip portion, which when tensioned, causes the distal tip portion 15 to deflect as is known in the art. A combination of deflection and rotation of the distal tip portion of the catheter provides steerability of the device. Another alternative for directability of the distal tip portion is to provide a micro-actuator (not shown) such as an element which expands or contracts upon application of an electrical current signal. Such an element can be substituted for the tension wire, for example.

As will also be appreciated, while the system is illustrated by the exemplary embodiment of a medical imaging system, these arrangements could be used in other devices, such as visual sensors in other devices, surveillance apparatus, and in other applications where a very small imaging device can be useful.

Moreover, with reference to all of the embodiments described herein, the device contemplated can be very small in size, and accordingly the imaging array of the SSID can have a lower pixel count than would otherwise be desirable. As technology advances, pixel size can be reduced, thereby providing clearer images and data. However, when using a lower number of pixels in an imaging array, the resolution of the image provided by the device can be enhanced through software in processing image data received from the SSID. The processor shown in FIG. 1, can be appropriately programmed to further resolve a scanned image from an array of an SSID, for example, based on information received as the SSID is moved slightly, such as from controlled vibration. The processor can analyze how such image data from the imaging array is altered due to the vibration, and can refine the image based on this information.

Figure 3:
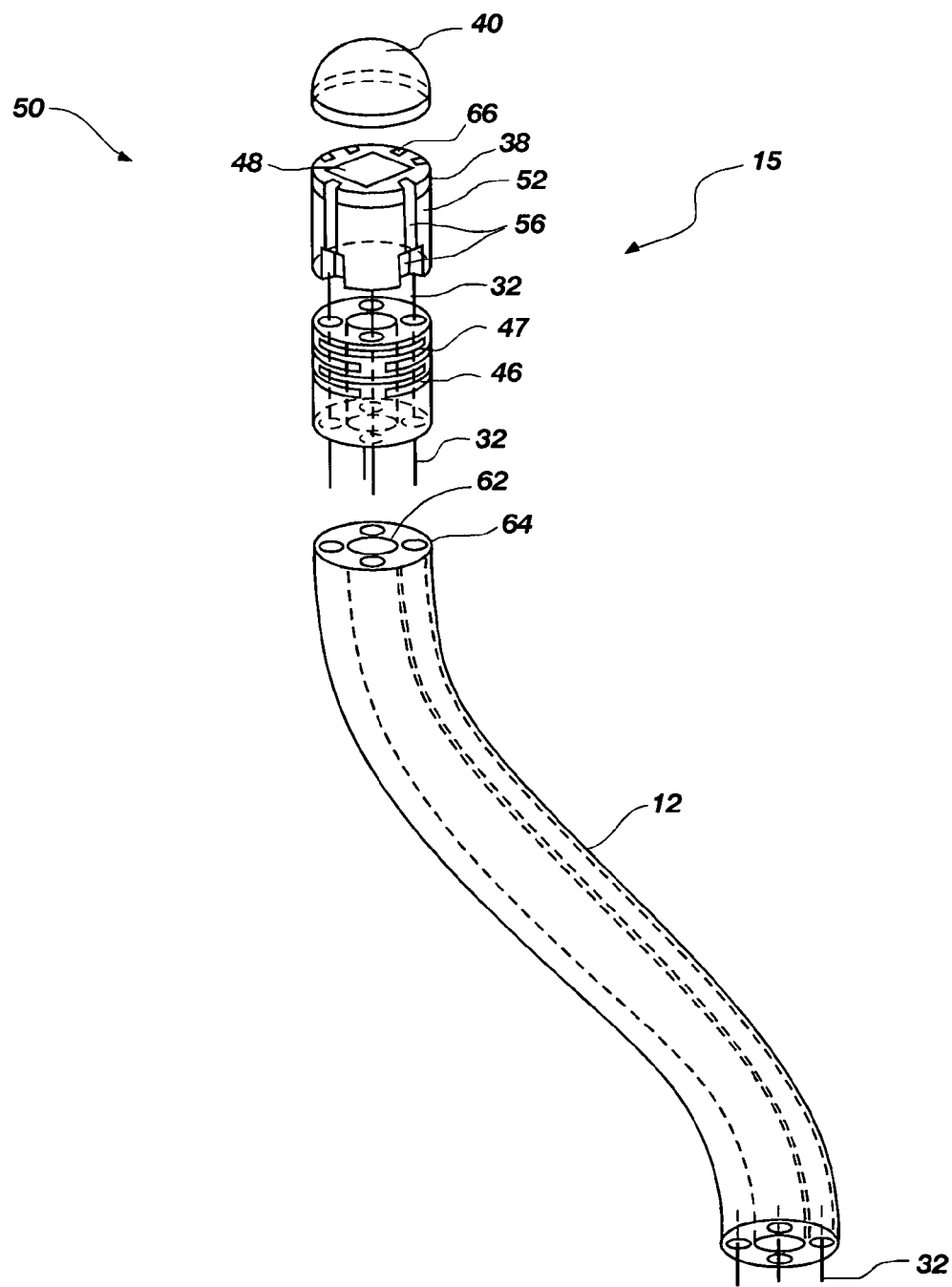
FIG. 3 is a perspective exploded view of another exemplary embodiment of the invention.

With reference to FIG. 3, in another embodiment, shown generally at 50, the catheter 12 can comprise an extruded tubing section having a central lumen 62 and a plurality of auxiliary lumens 64 disposed around the periphery of the central lumen. With this arrangement, imaging fluid can be conveyed to the distal tip portion 15 of the catheter via the central lumen or one or more of the auxiliary lumens. The central or auxiliary lumens can also carry a conductive line, such as conductive wires 32, that are configured to provide electrical signal, power, ground, and/or control to and from the SSID 38. Electrical signal is carried from the umbilical to the SSID via conductive strips 56 present on an adaptor 52. The conductive strips provide an electrical connection between electrical wires of the umbilical and the SSID. The conductive strips can be comprised of conductive metals, a conductor layed down on a captain strip as previously described, or can be insulated wire or non-insulated wires, as appropriate. In this embodiment, the SSID includes light-emitting diodes (LEDs) 66 configured to illuminate the area immediately adjacent the distal tip portion, and an imaging array 48.

As mentioned, electrical connections and mounting of the SSID 38 is facilitated by an adaptor 52. The adaptor carries the SSID 38 and is bonded to the remainder of the catheter, including a micromachined segment 46. A lens 40 is provided that can be bonded to the SSID 38. The lens can be configured to focus an image at a focal plane of the imaging array 48, or it can simply protect the SSID 38 and any filter or additional optical element used. Non-conductive, optically clear adhesive or epoxy can be used to bond the chip to the lens.

The micro-machined segment 46 includes transverse slots 47 cut into the tubing in an alternating pattern as shown in the Figure to provide for increased flexibility at the distal tip portion 15 of the catheter 12. Additional details on construction of similar slotted micro-machined tubing and segments can be found in U.S. Pat. No. 6,428,489, which is incorporated herein by reference. The micro-machined slots can intersect the auxiliary lumens 64, and can even be made deep enough to intersect the central lumen 62. This allows for transfer of fluid from within the catheter 12 through the slots to the area immediately adjacent the distal tip portion of the catheter. As discussed, this can be used to provide for delivery of an imaging fluid, such as a clear saline, and/or medicament for treatment of an area of anatomy adjacent the distal tip portion when the catheter is positioned within the anatomy of a patient. It also provides the possibility for body fluids adjacent the distal tip portion to be withdrawn for sampling through one or more of the lumens of the catheter.

In another embodiment, tensioning wires (not shown) can be threaded through the auxiliary lumens 64 of the catheter and attached to the proximal end of the adaptor 52. By providing a more flexible segment of the catheter tubing and along with tensioning wires, the distal tip portion 15 of the catheter 12 can be made directable by applying tension to one or more of the tensioning wires to deflect the tip of the catheter in a desired direction as is known in the art. In one embodiment, the tensioning wires can be the electrical wires 32 of the umbilical, which can be configured for transferring power, control, ground, and/or image signals along the catheter 12 to and from the distal tip portion 15.

Figure 4:
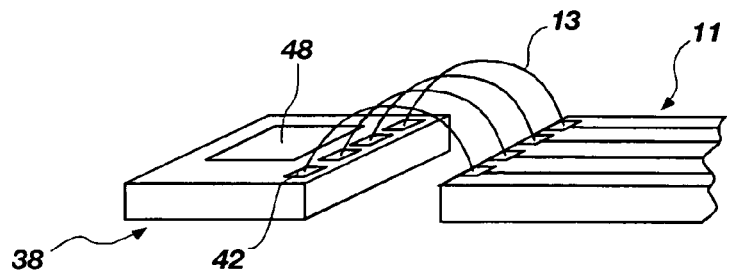
FIG. 4 is a schematic perspective illustration of a conventional wire bonding connection system consistent with the prior art.

With reference to FIG. 4, the conventional way of providing electrical connection between a conductive pad 42 on an SSID 38 and another structure 11 is by means of wires 13 soldered or bonded thereto. This connection method is known as wire bonding. The connection thus made is inherently fragile and susceptible to damage, particularly if the SSID is able to move with respect to the other structure. Such movement induces flexing and stress on the delicate wires and could cause breakage, or an undesired short between two or more wires.

Figure 5:
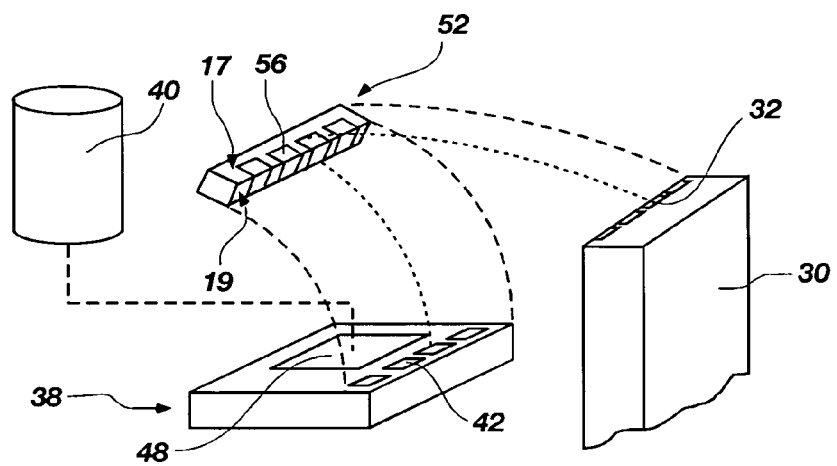
FIG. 5 is an exploded schematic perspective illustration of an embodiment of the connector system in accordance with the present invention.

With reference to FIG. 5, in contrast, a connector block or adaptor 52 of the invention provides for mechanical attachment as well as electrical connection. In other words, a connector body or bulk of the adaptor provides both stabilization and bonding between the SSID 38 and an umbilical 30, as well as an electrical connection.

The adaptor 52 comprises, in the exemplary embodiment shown, a block of nonconductive substrate material incorporating conductive strips 56 which bridge around a corner between a first surface 17 configured for bonding with an umbilical 30, and a second surface 19 configured for bonding with the SSID 38. The conductive strips are configured to be in alignment with conductive wires 32 on the umbilical and conductive pads 42 on the SSID. A lens 40 is shown as it would be optically coupled to the SSID. Though the adaptor is shown as bonded to an umbilical, other structures can also be bonded to the SSID by the adaptor, such as another chip, a board or other substrate upon which the chip is mounted, a conductive strip, a connector further coupled to an additional structure such as a wire strip or cable, a flexible strip having conductors thereon, etc.

Figure 6:
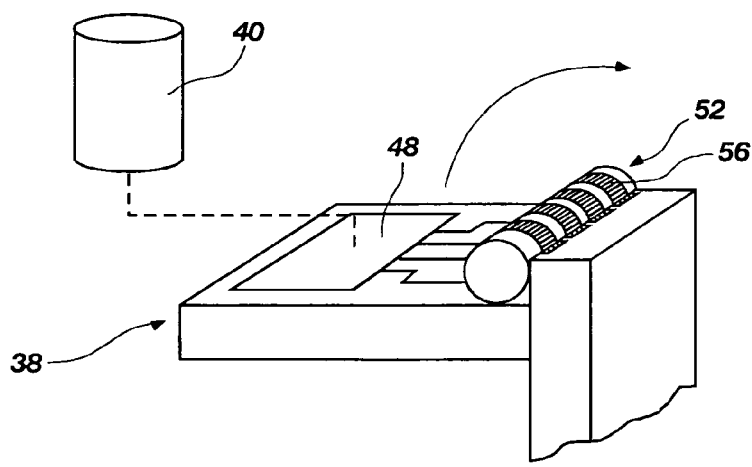
FIG. 6 is a schematic perspective illustration of an embodiment of the connector system in accordance with the present invention, wherein the SSID is movable for viewing various angles with respect to the umbilical.

With reference to FIG. 6, instead of providing a rectilinear adaptor 52, a circular cross-section or cylindrical adaptor can be provided. Good contact between the adaptor, the conductive pads (not shown) on the SSID 38, and conductive strip 56 is provided by applying pressure and deforming the conductors slightly due to the round shape of the connector body being pressed against the flat surfaces of the other structure. An epoxy, or other adhesive is used to bond the assembly together and fills in the gaps around the cylindrical body. Again, the SSID includes an imaging array 48, and a lens 40 can be configured to be optically coupled to the imaging array.

Figure 7:
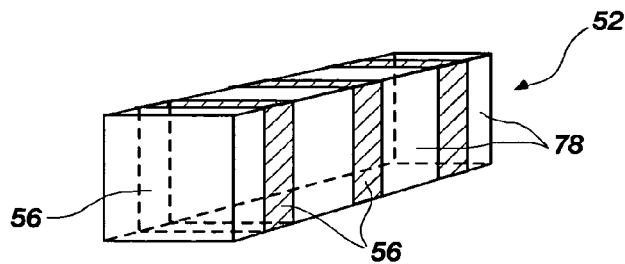
FIG. 7 is a perspective view of an adaptor incorporating conductive pathways in one embodiment.

With reference to FIG. 7, a connector block or adaptor 52 can have a conductive pathway all the way around its body or substrate 78. For example, conductive strips 56 of conductive material can be deposited on the surface by lithographic masking deposition or other known techniques, or the adaptor can be formed by laying up a laminate of conductive and nonconductive materials, and thereafter machining out blocks transverse to the plane of the lay-up to form the bulk body or substrate of the adaptor. The adaptor can then have conductors disposed on the surface, as the conductive layers are exposed on all the surfaces all the way around the connector body. It will be appreciated that having the conductors interconnect locations on surfaces all the way around the counter block can be useful. For example, in one application of this embodiment, the adaptor can be used in any rotational orientation around its lengthwise axis.

Figure 8:
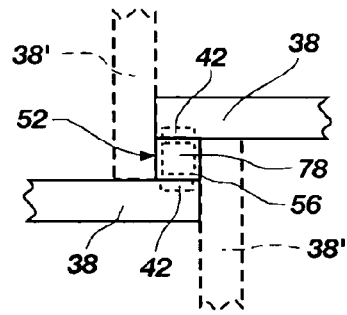
FIG. 8 is a schematic side view illustration of a connection between two chips, such as SSIDs, including the adaptor of FIG. 7.

With reference to FIG. 8, it will be appreciated that an adaptor 52 such as that discussed in FIG. 7 can be useful in connecting chips and other structures in a variety of ways. Specifically, an adaptor 52, including a substrate 78 having a conductive strip 56, connects two opposite surfaces of the adaptor. In the embodiment shown, two devices, such as two SSIDs 38, each have conductive pads 42. Both the conductive pathway between the conductive pads of the SSIDs and a mechanical bond between the two SSIDs can be formed as shown. A number of alternate configurations are possible, as that shown in outline where two SSIDs 38 are connected to the adaptor in an alternative configuration.

Figure 9:
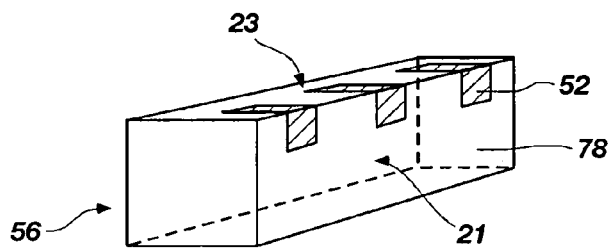
FIG. 9 is a perspective view of an adaptor incorporating conductive pathways in another embodiment.

With reference to FIG. 9, an adaptor 52 can include a substrate 78 incorporating conductive strips 56 configured as discussed above, each having a conductive pathway from a first side surface 21 to a second side surface 23. The conductive strips can be to those discussed above, which are deposited on the connector body by a masking process, a lithography process followed by etching, or by a number of other ways to form such conductive strips. In another embodiment, the conductors can be formed by machining, etching, or otherwise removing material from the substrate 78 to form slots (not shown) therein. The slots can afterwards be filled with conductive material, and the conductor block can be machine finished to a final shape leaving exposed surfaces of the material in each slot.

Figure 10:
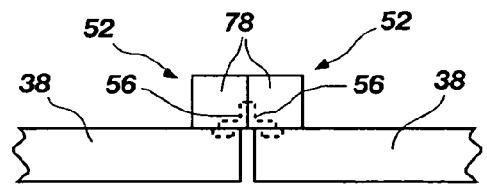
FIG. 10 is a schematic side view illustration of a connection between two chips, such as SSIDs, including the adaptor of FIG. 9.

FIG. 10 depicts two SSIDs 38 (or other multiple chip interfaces) having conductors such as conductive pads 42, which can be connected by two adaptors 52, each having conductors conductive strips 56 providing a conductive pathway between at least two sides. The substrates 78 or each respective adaptor can then be bonded together so that the conductors meet and provide a conductive pathway. In another embodiment, the conductors can be bonded together first and then together bonded to two chips to form a connection. An additional block which bridges across the two connector bodies can be employed in one embodiment to further enhance the mechanical connection, such as by bonding it to and across the connector blocks.

Figure 11:
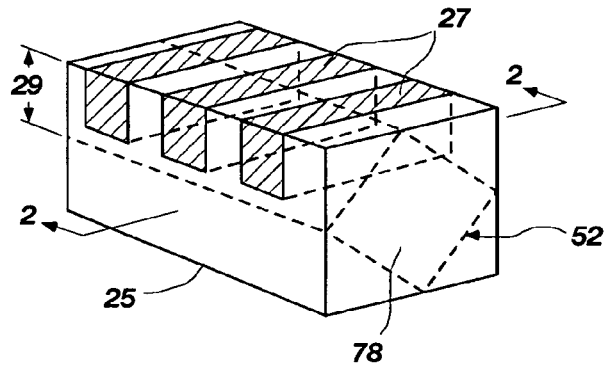
FIG. 11 is a schematic perspective illustration of a fabrication technique for modifying a connector body to form a pathway through an interior portion, thereby forming an adaptor, the adaptor being not yet cut free, but shown in outline form within a larger preform block of material.
Figure 12:
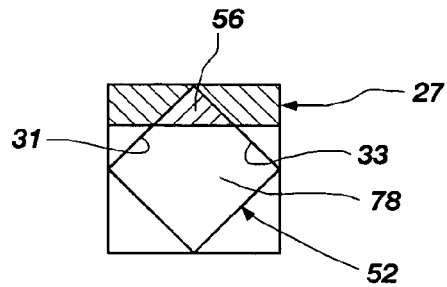
FIG. 12 is a side cross-sectional view of a connector body as shown in FIG. 11 taken along line 2-2.

With reference to FIGS. 11 and 12, further discussion of additional ways to make further embodiments of the invention include starting with a preform block 25 formed of a nonconductive material. Conductive pathways will be created by altering the block at certain locations. For example, the preform can be masked and altered with conductive material 27 as shown, such as by introducing a conductive material into the preform block by crystal diffusion. The mask might simply be a series of long strips and the preform cut be from a flat substrate after the crystal diffusion process. The material of the preform is altered is to a depth 29; and thereafter, the adaptor 52 is machined from the preform. A resulting adaptor 52 has a substrate 78, and a conductive body or strip 56 where the material has been modified intersects a first surface 31 and a second surface 33.

In another embodiment the preform may simply be slotted, such as by using a chip fabrication saw to form the slots of desired width and depth. Thereafter, the slots can be filled with a conductive material. When the conductor material is hardened, the adaptor 52 can be machined free from the preform 25 and the resulting configuration is similar to that described above.

Figure 13:
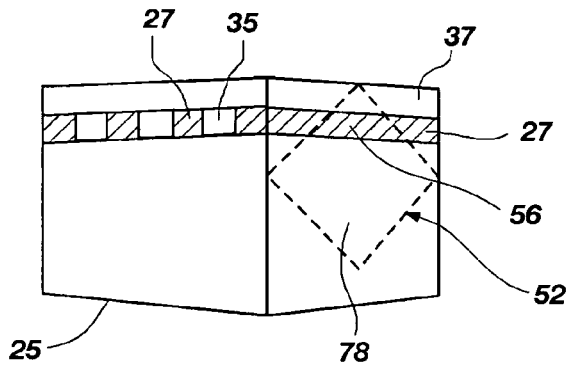
FIG. 13 is a schematic perspective illustration of another fabrication technique for forming an adaptor having conductive pathway(s) through an interior portion thereof, showing a preform block constructed in accordance with one embodiment, the connector body to be formed therefrom being shown in outline.
Figure 14:
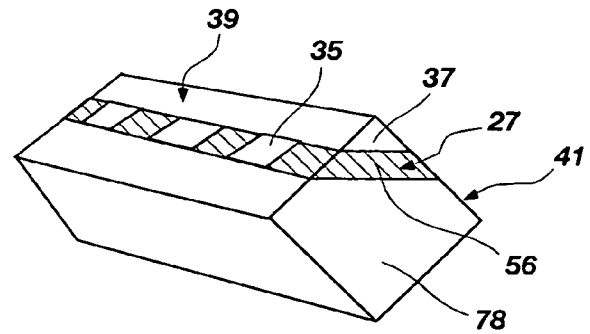
FIG. 14 is a perspective view of a connector body of FIG. 13 after machining from the block.

With reference to FIGS. 13 and 14, in another embodiment, the connector body is formed by laying up a laminate configuration having a nonconductive substrate which is overlaid by a layer comprising long strips of conductor material 27 and nonconductive material 35 disposed alternately to provide discrete conductive paths. This is overlaid by a further layer 37 of nonconductive material. It will be understood that the adhesive, or other method used to form the lay-up, will depend on the material. However, conventional bonding using adhesives such as solvents, welding, and the like, can be used.

In another embodiment, the configuration can be formed by forming grooves in the preform block 25 filling the grooves with the conductive material 27 to form the conductors, and then overlaying this with another layer of nonconductive material 37. For example, a ceramic substrate could be provided with grooves filled with an emollient conductor, and then can be lapped flat after the conductor hardens. The top layer, also formed of ceramic, can then be bonded thereto by adhesive. After the preform block has been completed, the adaptor 52 can be cut free by micro-machining, grinding, etc. The resulting adaptor can then include the adaptor substrate 78, and conductive pathways, via conductive strips 56, from a first surface 39 to a second surface 41.

Figure 15:
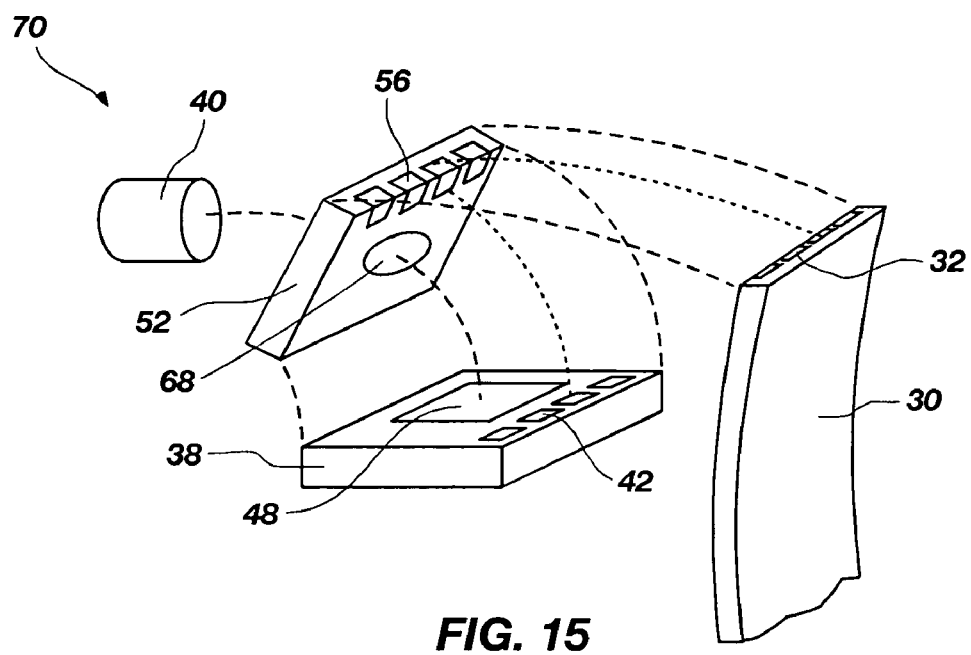
FIG. 15 is a perspective exploded view of another exemplary embodiment of the invention, wherein connector block also supports the lens.
Figure 16:
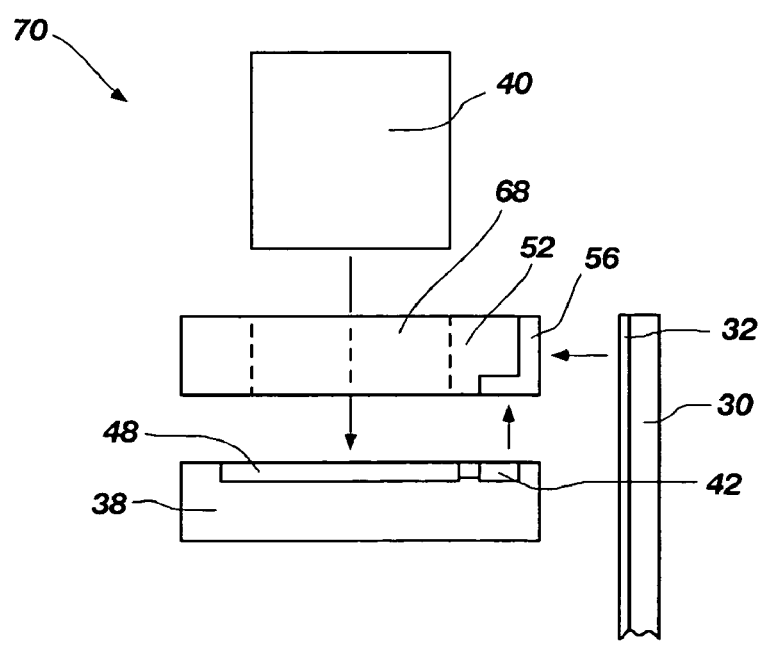
FIG. 16 is a cross sectional exploded side view of the exemplary embodiment of FIG. 15.

Referring now to FIGS. 15 and 16, an alternative system, shown generally at 70, includes a lens 40, such as a GRIN lens, that is optically coupled to an imaging array 48 of an SSID 38. In one embodiment, the lens can be coupled to the imaging array by a clear adhesive material. Conductive pads are also present on the SSID and are configured to provide electrical signal, power, ground, and/or control to and from the SSID.

The SSID 38 can comprise a silicon or silicon-like substrate or amorphous silicon thin film transistors (TFT) having features typically manufactured therein. Features including the imaging array 48, the conductive pads 42, metal traces (not shown), circuitry (not shown), etc., can be fabricated therein. With respect to the conductive pads, the connection between conductive pads and the adaptor 52 can be through soldering, wire bonding, solder bumping, eutectic bonding, electroplating, and conductive epoxy. However, with this configuration, a direct solder joint having no wire bonding between the conductive strips and the conductive pads can be preferred, as good steerability can be achieved with less risk of breaking electrical bonding. The same is true with respect to the electrical connection between the electrical wires of the umbilical and the conductive strips of the adaptor. In one embodiment, the umbilical can provide power, ground, clock signal, and output signal to the SSID through the adaptor. Other integrated circuit components can also be present for desired applications, such as light emitting diodes (LEDs) (not shown) for providing light to areas around the GRIN lens. If LEDs are present on the SSID, the adaptor can be of a clear material to allow light to pass therethrough. As the above described component are exemplary, it is not required that all of these components be present, as long as there is a visual or photon data gathering means, and some means of converting that data to a visual image or a visual reconstruction. The SSID can be any solid state imaging device, such as a CCD, a CID, or a CMOS imaging device.

The lens 40 can be a GRIN lens coated with an opaque coating on the curved surface to prevent light from entering the lens at other than the flat surface that is most distal with respect to the SSID. Alternatively, as the lens 40 is supported by an adaptor 52 having an opening 68, the adaptor can provide a similar function as provided by the opaque coating.

The adaptor 52 includes four conductive strips 56 that are configured to electrically communicate in an "around the corner" configuration. The conductive strips are positioned to contact the conductive pads 42 on the SSID 38, once the adaptor and the SSID are mated together. In this configuration, an umbilical 30 containing conductive wires 32 can be electrically coupled to the conductive strips. When assembled, by innervating the conductive strips with the conductive wires, the conductive pads are thus energized, thereby providing power, signal, ground, and/or control to and from the SSID.

Figure 17:
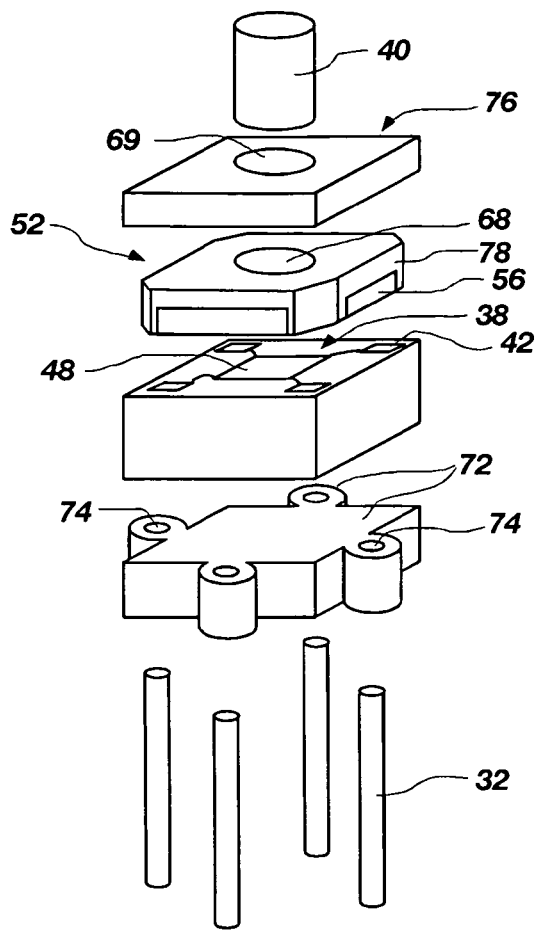
FIG. 17 is a perspective exploded view of another exemplary embodiment of the invention.
Figure 18:
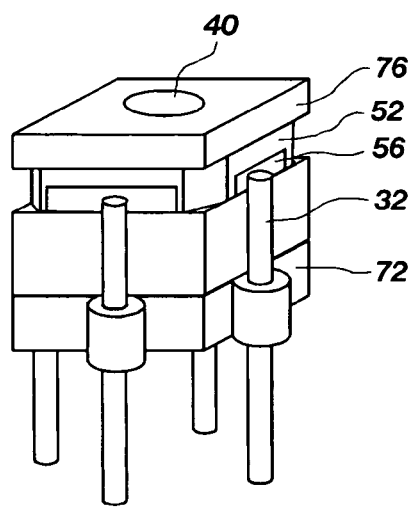
FIG. 18 is a perspective assembled view of the exemplary embodiment of FIG. 17.

Turning now to FIGS. 17 and 18, a lens 40 is supported by a connector block or adaptor 52, and a supplemental lens holder 76. The adaptor and the supplemental lens holder are configured to accept and hold the GRIN lens via respective openings 68, 69. The adaptor can comprise two different materials. A first material can be a non-conductive material that forms the substrate 78. The substrate supports one or more conductive strips 56 formed of an electrically conductive material, such as a metal. The conductive strips act to provide electrical contact between an umbilical, which comprises insulated conductive wires 32 in this embodiment, and conductive pads 42 present on the SSID 38. The conductive wires can be coupled to the conductive strips using a conductive bonding material, such as silver or gold filled epoxy, silver or gold solder, or another suitable adhesive or eutectic conductive substance.

Each of the conductive wires 32 can also be supported in a proper position by a wire guide 72, and more specifically, by feeding each wire through lumens 74 defined by the wire guide. The conductive wires provide electrical contact through an umbilical between the adaptor 52 (and ultimately the SSID chip) and a computer interface (not shown), linking the SSID with another structure, e.g. a power source, signal processor, ground, or controller (not shown). The conductive wires can also be used as tensioning wires to provide steerability. However, this is not required, as other means of controlling the direction of pointing of a head of the camera can be implemented.

Each of the conductive strips 56 is configured to transfer current from a location on a side of the adaptor 52 to a location on a bottom surface of the adaptor. More detail concerning the conductive strips can be appreciated with reference to FIGS. 19 and 20. Still referring to FIGS. 17 and 18, the conductive pads 42 are electrically coupled to an imaging array 48 of the SSID 38. Additionally, each of the conductive wires 32 are electrically coupled to a corresponding conductive strip 56. Thus, by alignment of the conductive strips with the conductive pads, when the adaptor is mated to the SSID, electrical power and data signals can be sent to and from a source (not shown), through the conductive wires of the umbilical, through corresponding conductive strips, through corresponding conductive pads, and to and from the imaging array.

Figure 19:
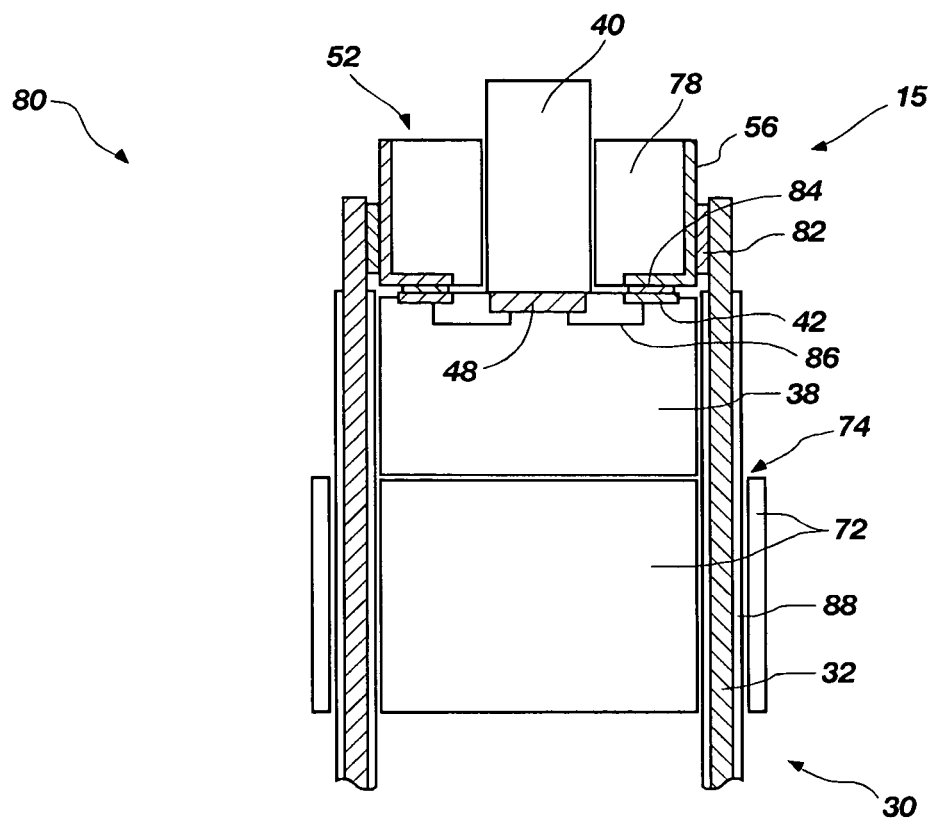
FIG. 19 is a cross sectional view of another exemplary embodiment of the invention.
Figure 20:
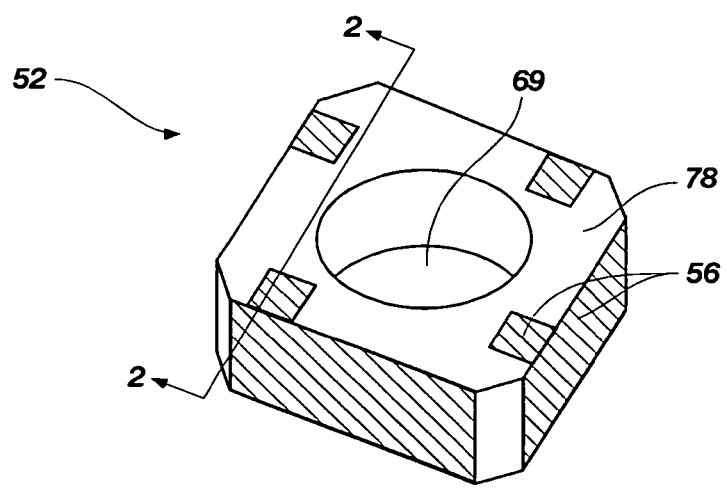
FIG. 20 is a perspective view of an adaptor or connector block of FIG. 19.

Referring now to FIGS. 19 and 20, a system shown generally at 80, includes a distal tip portion 15 of an imaging catheter comprising a lens 40, such as a GRIN lens. The lens is supported laterally by a connector block or adaptor 52. A supplemental lens holder as described previously can also be used, but is not present in this embodiment. Again, the adaptor has a dual function, including providing support for the lens, and providing electrical communication between an electrical umbilical 30 and an SSID 38. The adaptor typically includes a non-conductive substrate material 78 and a conductive strip 56. The non-conductive substrate material can be a refractory and/or polymeric material such as SU-8 polymer material manufactured by IBM, Foturan which is a photosensitive glass manufactured by Corning, polymethyl methacrylate (PMMA) molded by Lithographie Galvanoformung Abformung (LIGA), or oxidized deep reactive ion etched (DRIE) silicon. In one embodiment, the material can be substantially transparent so that verification of bonding of the adaptor to the SSID can be more easily obtained by visual inspection, such as by a microscope. If the SSID has a light source, such as an LED incorporated in it, the transparent block material enables the transmission of light forward. Conductive strips, as mentioned, are also attached to the adaptor, and thus, a path of electrical conductivity can be effectuated around a corner from a side surface to a bottom surface of the adaptor. Central aperture 69 for supporting the lens is also included in the adaptor.

An electrical umbilical 30, including conductive wires 32, can comprise an insulator coating portion 88. The conductive wires are supported by a wire guide 72 having multiple lumen 74. In this embodiment, the insulator coating portion is removed adjacent the distal ends of the wires. This is done to provide a means of contacting the conductive wires 32 with the conductive strips 56, so that electrical contact and communication can be provided between the SSID 38 and the power source, controller, and/or processor (not shown) through the conductive wires. In this embodiment, each conductive wire is attached to a conductive strip at a side surface, and is held in electrical contact therewith by a conductive bonding material 82 that can be used to electrically couple two conductive lines, such as that discussed above.

At the bottom surface of the adaptor 52, the conductive strip 56 also contacts the conductive pad 42 of the SSID 38. This contact is also fixed by the use of a conductive bonding material 84, such as that described previously. The SSID can comprise an imaging array 48, additional I.C. elements (not shown), conductive pads, and an electrical connection 86 between the connective pads and the imaging array. Additionally, the SSID can further include a microprocessor as well as light sources, such as LED's, as described above.

The lens 40 can be in close proximity or in contact with the imaging array 48 as the lens directs and focuses light or photons onto the imaging array. The conductive wires 32 (two of which are not shown in a four wire umbilical system), can provide the dual function of guiding the direction the SSID, as well as provide electrical contact between any power source/signal processors (not shown) and the SSID at distal tip 15 of the catheter, though this dual functionality is not required. For example, steering can be by a micromachined tube, as is known in the art.

The components of a miniature imaging device can be fused together or bonded together as desired. For example an epoxy, such as a UV cure epoxy, can be used to bond the lens 40 to the imaging array 48 of the SSID 38. However, with the use of such epoxy, care should be taken to not use a UV light at an intensity that would damage the SSID or other structures of the device. Other locations where an epoxy or other bonding material can be used to hold components together include the interface between the lens and the adaptor 52, the interface between the substrate of the SSID and the wire guide 72, and between the wire guide and the electrical umbilical 30 (which may or may not also act as tensioning wires). The wire guide can also be bonded to the rest of the catheter (not shown) in this manner.

The particular construction of the embodiments above are facilitated by the very small adaptor 52 that not only acts hold the lens 40 in place over an SSID 38, but also provides a conductive path for transporting electrical power, ground, control, and/or data signals from the conductive wires adjacent a side surface to the conductive pads 42 on the SSID. However, the adaptor provides other advantages. For example, with this configuration, positioning and alignment of the lens on the SSID is more easily accomplished. This is particularly true since the size of this imagine device can be made smaller than about 0.5 mm in total width. Additionally, because the wires are attached to the adaptor on a side surface, there is no need to bend the electrical wires. This provides better strength and easier assembly for the connections for the wires, and for the miniature-imaging device as a whole. Thus, in this embodiment, the configuration of the adaptor facilitates the manufacturing of a very small imaging device.

Turning now to how such an adaptor 52 can be fabricated in one embodiment, FIGS. 21a-h depict the manufacture of two adaptors. This is shown as exemplary, as one can be made individually, or alternatively, more than two can be made together, either by the process described below or by other known chip manufacturing processes. The figures are shown in cross section, and one of the two adaptors is shown along line 2-2 of FIG. 20. FIGS. 21a-h will be discussed collectively and sequentially.

Figure 21A:
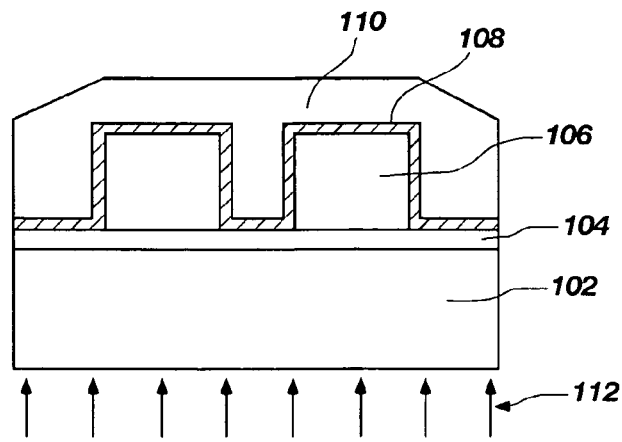
FIGS. 21a to 21h provide cross-sectional representations of two adaptors at various preparative stages.
Figure 21B:
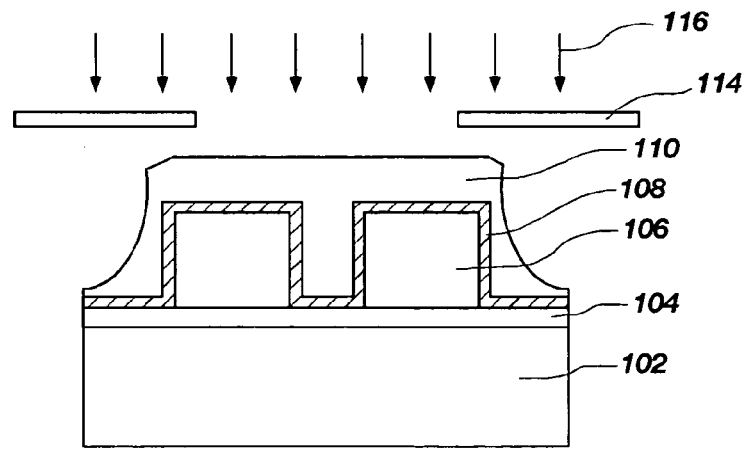

With reference to FIG. 21a, a substrate 102 is provided that will be used to make an adaptor. The substrate can be, for example, a silicon wafer. To the substrate is applied or grown a removable layer 104. If the substrate 102 is a silicon wafer, then the removable layer 104 can be a thermal silicon dioxide layer. An appropriate thickness can be about 0.5 microns. This provides a working base to fabricate one or more primary lens holders.

A polymer layer 106, such as SU-8 manufactured by IBM, can be spun onto the silicon dioxide layer having a desired thickness dimension. Next, the layers are selectively exposed to UV light, in the presence of a mask, to form desired structure. These polymer blocks can each become the substrate of an adaptor. An example size can be a structure having a height of 300 microns, a length of 360 microns and a width of 380 microns. The center aperture that will hold the lens can be about 300 microns in diameter. Thus, if the length is 360 microns, and the aperture is 300 microns in diameter, a 30 to 35 micron distance between the edge of the aperture and the edge of the polymer is all that may be present in this embodiment. The dimensions above are given by way of example. However, larger and even smaller blocks can be fabricated in accordance with the methods described herein.

On top of the polymer 106, a metal trace material 108 is sputtered or evaporated at an appropriate thickness. The metal trace material will ultimately become the conductive strip. Gold, for example, can be used as the metal trace material. Additionally, the appropriate thickness of the deposited metal trace depends upon the size of the SSID being made. However, commensurate with the present example, a thickness of about 0.5 microns can be used.

Figure 21C:
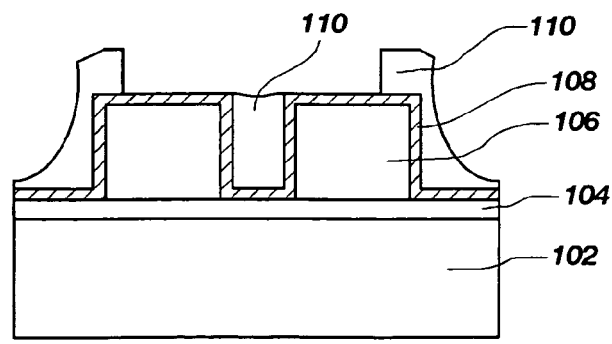

A photoresist material 110 can now be added atop the metal trace material. The photoresist material can be any material that can be altered when exposed to energy, such as heat and UV light. Further, the photoresist material can be diluted to achieve a desired result, depending on the application. In one embodiment, a photoresist material can be used that is sensitive to heat by way of evaporation of a solvent. The UV light can be used to selectively expose the photoresist such that the UV exposed photoresist can be developed away in a developer (using positive photoresist), or the underexposed photoresist can developed away in a developer (using negative photoresist). As different thicknesses are present, the photoresist can evaporate off at different speeds, leaving the photoresist material configured such as that shown in FIG. 21b. Depending on the photoresist material used, the thickness differential can be as much as 10 fold or more, e.g., 2 microns in some areas and 20 microns in other areas. Once the photoresist material 110 is configured as desired, then from a direction opposite the substrate 102, the photoresist material can be exposed to UV light 116. A photomask 114 can be used such that only a discrete desired portion of the photoresist material is developed as shown in FIG. 21c. Additionally, only the thinner portion of the photoresist material, i.e., the top portion, is removed at this time.

Figure 21D:
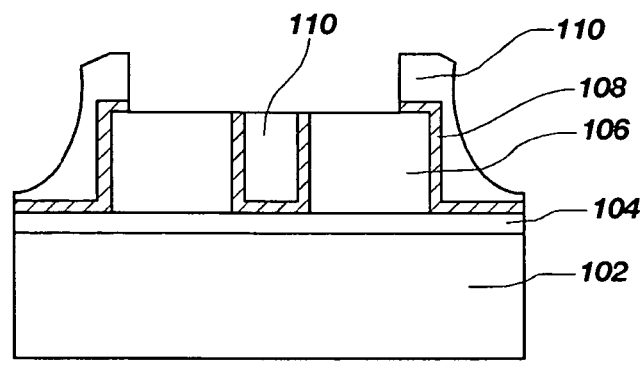
Figure 21E:
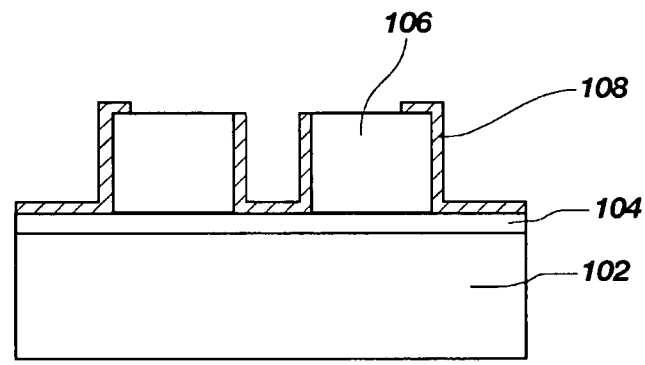

In FIG. 21c, the photoresist material is removed such that an exposed section of the metal trace element can be removed by, for example, wet etching or dry etching. FIG. 21d shows the state of the photoresist material after portions are removed as described above. Next, as shown in FIG. 21e, the photoresist material is completely removed. The photoresist material can be removed by using a material known to react with the chosen photoresist material. In one embodiment, acetone can be used to remove the photoresist material.

Figure 21F:
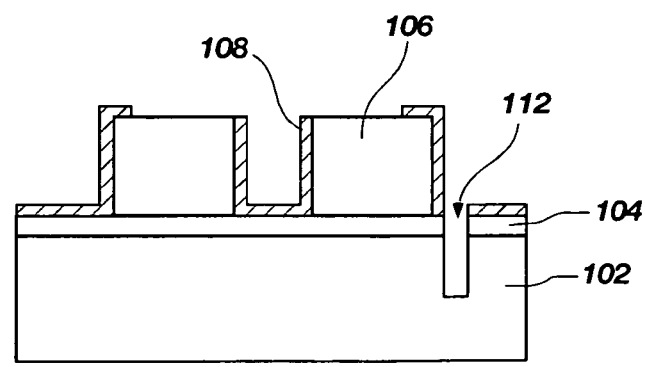
Figure 21G:
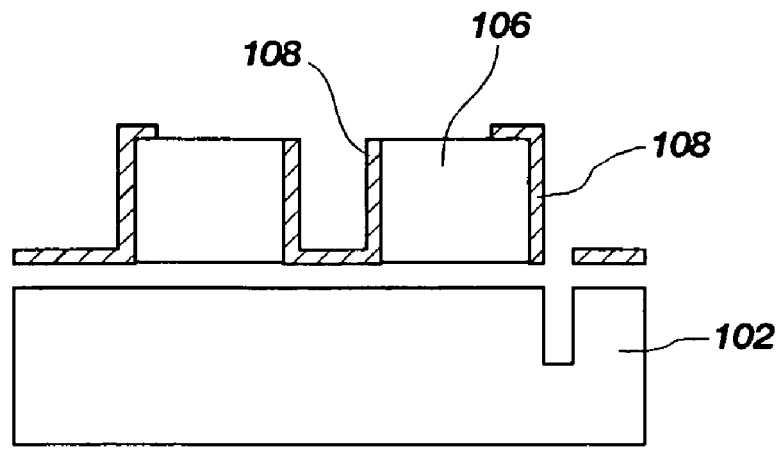
Figure 21H:
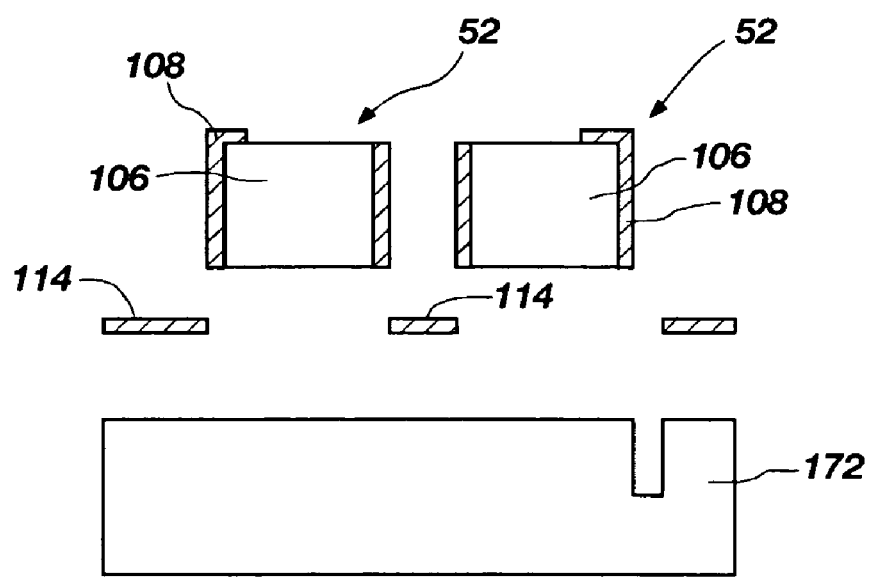

Next, shown in FIG. 21f, a saw cut 112 can be made into the substrate, e.g., approximately through half of the substrate using a chip fab saw, for example. This step creates an opening for removal of the removable layer 104, as shown in FIG. 21g. For example, if the removable layer 104 is silicon dioxide, then hydrofluoric acid (HF) can be used to react with the removable layer, releasing the polymer 106 from its connection with the substrate. Once the silicon dioxide has been removed, the metal trace sections 108 that are not adhered to the polymer 106 can be broken off as shown in FIG. 21h. Thus, two adaptors 52 remain separated from the substrate 102, each of which can be used in conjunction with a catheter borne SSID such as that described above.

The embodiments thus far shown depict GRIN lenses optically coupled to imaging arrays of SSIDs by a direct bonding or coupling. However, the term "optically coupled," also provides additional means of collecting light from GRIN lens and coupling it to an imaging array of an SSID. For example, other optical devices can be interposed between a GRIN lens and an SSID, such as a color filter, fiber optic, or any shape optical lens including a prism or wide angle lens. The fiber optic, or any shape optical lens including a prism or wide angle lens, can be placed on top of the GRIN lens in one embodiment.

In one embodiment, a system of converting monochrome imaging to color can be accomplished by utilizing a filter having a predetermined pattern, such as a Bayer filter pattern. The basic building block of a Bayer filter pattern is a 2×2 pattern having 1 blue (B), 1 red (R), and 2 green (G) squares. An advantage of using a Bayer filter pattern is that only one sensor is required and all color information can be recorded simultaneously, providing for a smaller and cheaper design. In one embodiment, demosaicing algorithms can be used to convert the mosaic of separate colors into an equally sized mosaic of true colors. Each color pixel can be used more than once, and the true color of a single pixel can be determined by averaging the values from the closest surrounding pixels.

Figure 22:
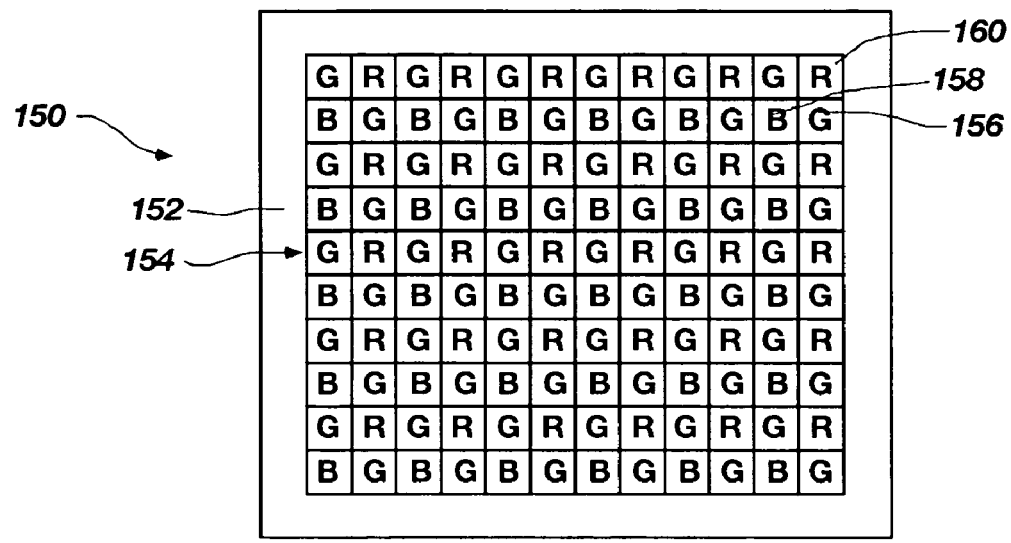
FIG. 22 is plan view along the optical axis of an exemplary color filter insert that can be used with imaging devices in accordance with principles of the invention.
Figure 23:
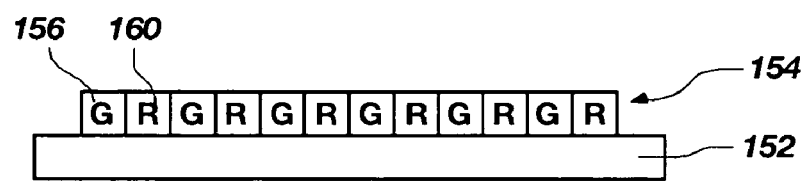
FIG. 23 is a side view of the color filter insert of FIG. 22.
Figure 24:
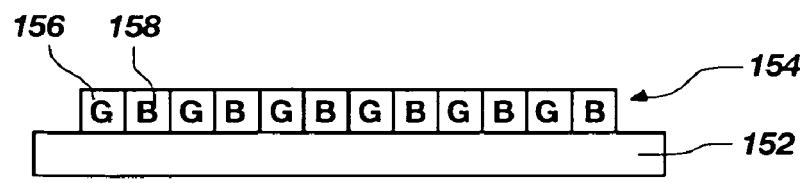
FIG. 24 is a second side view of the color filter insert of FIG. 22, taken at 90 degrees with respect to FIG. 23.

Specifically, with reference to FIG. 22-24, a color filter insert, shown generally at 150, can comprise a substantially optically clear filter substrate 152 and a color filter mosaic portion 154. The filter insert as a whole is made up of green transparent color material 156, blue transparent color material 158, and red transparent color material 160. Each of the transparent color material 156, 158, 160 can be polymerized color resins such as those available from Brewer Science. In one embodiment, the green color material 156 can be put down on the clear filter substrate first, then the red 160 and blue 158 color material can be positioned in the appropriate spaces provided by the green material. Each transparent color material can be configured to be the size of an SSID image array pixel. The optically clear filter substrate can be, for example, a polymeric material such as SU-8 available from IBM, having a thickness of about 20 microns, though other thicknesses and materials can be used.

Figure 25:
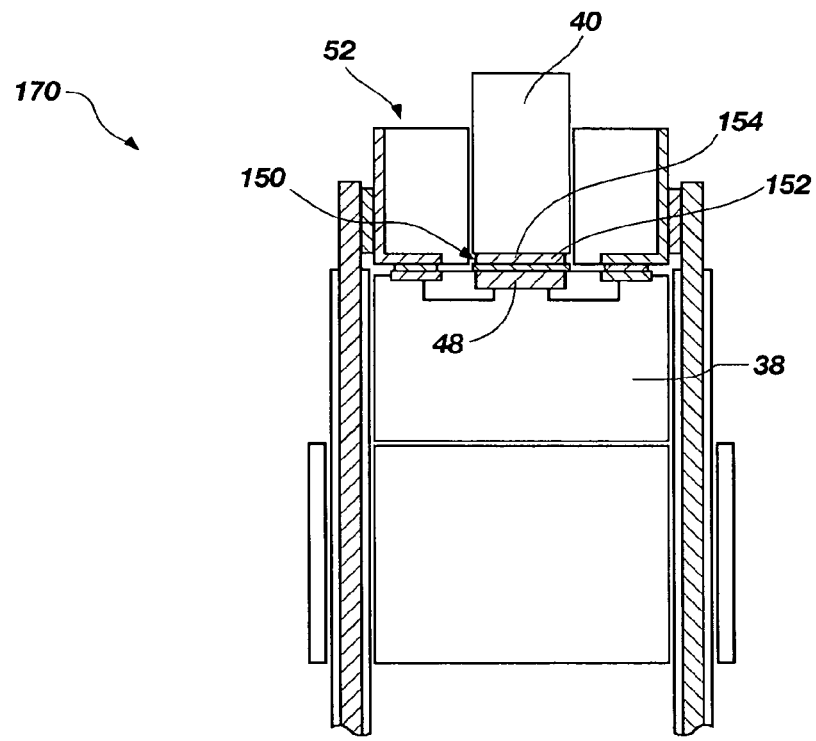
FIG. 25 is a schematic cross sectional representation of an example of a device similar to that shown in FIG. 19, having a color filter insert of FIG. 22 inserted therein.

Turning now to FIG. 25, a system 170, including a color filter insert 150 having an optical clear filter substrate 152 and the color filter mosaic portion 154, can be positioned between a lens 40 and an imaging array 48 of an SSID 38. Any bonding technique or mechanical coupling can be used to connect the SSID to the lens through the color filter insert or fiber optic in order to make the optical connection, such as bonding by an optically clear bonding epoxy. Other structures are shown in FIG. 25 that are similar to those described with respect to FIG. 19.

Figure 26:
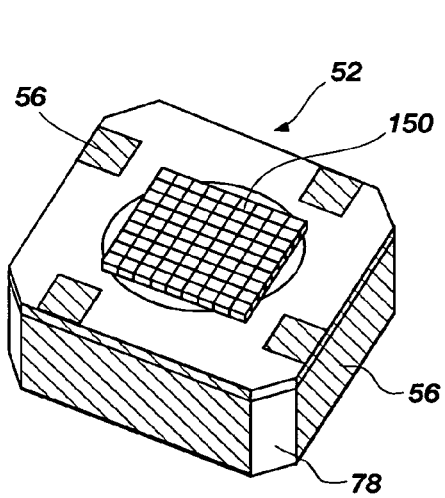
FIG. 26 is a bottom perspective view of an exemplary adaptor or connector block integrated with a color filter insert.
Figure 27:
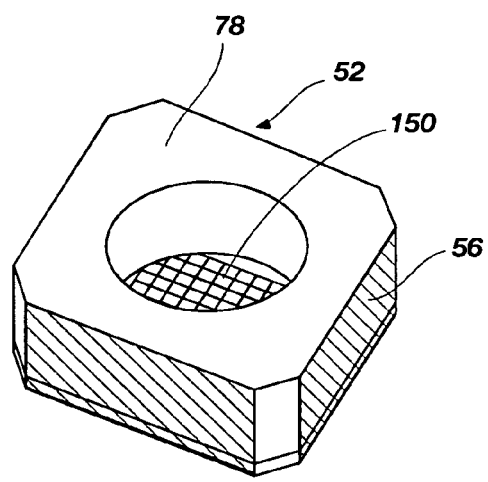
FIG. 27 is a top perspective view of an exemplary adaptor or connector block integrated with a color filter insert.

FIGS. 26 and 27 depict one possible relationship between a color filter insert 150 and an adaptor 52 (where the color filter can be integrated directly on the adaptor) from a bottom perspective view and a top perspective view, respectively. The adaptor includes a substrate 78 and conductive strips 56, as previously described.

As will be appreciated, an imaging device in accordance with principles of the invention can be made very small, and is useful in solving certain imaging problems, particularly, that of imaging a remote location within or beyond a small opening, for example in human anatomy distal of a small orifice or luminal space (anatomical or artificial, such as a trocar lumen), or via a small incision, etc. In fact, because of the solid state nature of the SSID, and the solid connection resulting from the use of an adaptor, these cameras can be made to be micron-sized for reaching areas previously inaccessible, such as dental/orthodontics, fallopian tubes, heart, lungs, vestibular region of ear, and the like. Larger lumens or cavities can be view with a greater degree of comfort and less patient duress, including the colon, stomach, esophagus, or any other similar anatomical structures. Additionally, such devices can be used for in situ tissue analysis.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A stacked, miniaturized imaging device, comprising:
a first layer comprising a substantially planar support member having at least two alignment apertures disposed on opposing sides thereof, the alignment apertures being oriented to position attached conductive wires approximately perpendicular to a top surface of the support member;
a second layer disposed on top of the first layer and comprising a substantially planar chip substrate having at least one imaging array disposed thereon and conductive contact points disposed coplanar with a light receiving surface of the chip substrate;
a third layer comprising a lens adaptor disposed on top of the second layer, the lens adaptor comprising conductive contact points disposed on an outer side surface of the lens adaptor and continuously extending to a bottom surface of the lens adaptor; and
at least one conductive wire disposed within each alignment aperture and positioned to align the three layers in a stacked configuration, the conductive wires extending longitudinally along a corresponding side surface of the chip substrate and the lens adaptor.

2. The stacked, miniaturized imaging device of claim 1, wherein the lens adaptor comprises a single unitary member in direct contact with the light receiving surface of the chip substrate.

3. The stacked, miniaturized imaging device of claim 1, wherein the conductive wires are bonded directly to the lens adaptor.

4. The stacked, miniaturized imaging device of claim 1, wherein the lens adaptor is substantially rectangular in shape having a hollow barrel disposed approximately in the center of the rectangle.

5. The stacked miniaturized imaging device of claim 1, wherein the alignment apertures are configured to direct the conductive wires to an outer side surface of the lens adaptor.

6. The stacked miniaturized imaging device of claim 1, wherein the alignment apertures are oriented parallel to a longitudinal axis of the chip substrate.

7. The stacked miniaturized imaging device of claim 1, wherein the lens adaptor is shaped to approximate the shape of the chip substrate.

8. The stacked miniaturized imaging device of claim 1, wherein the conductive wires extend across an outer surface of the chip substrate.

9. The stacked miniaturized imaging device of claim 1, wherein the alignment apertures are positioned on a side surface of the support member.

10. The stacked miniaturized imaging device of claim 1, wherein the third layer further comprises a GRIN lens disposed within the lens adaptor.

11. A stacked, miniaturized imaging device, comprising:
a first layer comprising a support member having at least one alignment aperture disposed therein, the alignment aperture being oriented to position at least one conductive wire approximately perpendicular to a top surface of the support member;
a second layer disposed on top of the first layer and comprising a chip substrate having at least one imaging array disposed thereon and associated electrical conductive contact points positioned coplanar with a light receiving surface of the chip substrate;
a third layer comprising a lens adaptor disposed on top of the second layer, the lens adaptor being configured to house a GRIN lens therein and further comprising at least one electrical conductive contact point disposed on an outer side surface of the lens adaptor, the at least one electrical conductive contact point continuously extending from a side surface of the lens adaptor to a bottom surface of the lens adaptor; and
at least one conductive wire disposed within the alignment aperture and positioned to align the three layers in a stacked configuration, the conductive wire extending longitudinally along a corresponding side surface of the second and third layers and contacting the at least one electrical conductive contact point disposed on the outer surface of the lens adaptor.

12. The stacked miniaturized imaging device of claim 11, wherein the GRIN lens is the distal most optical component of the miniaturized imaging device.

13. The stacked miniaturized imaging device of claim 11, wherein the support member comprises at least two alignment apertures disposed on opposing sides of the support member.

14. The stacked miniaturized imaging device of claim 11, wherein the support member is substantially planar.

15. The stacked miniaturized imaging device of claim 11, wherein the longitudinal direction of the alignment aperture is substantially parallel to the longitudinal direction of an image plane of the chip substrate.

16. A stacked, miniaturized imaging device, comprising:
a first layer comprising a substantially planar support member having at least two alignment apertures disposed on opposing sides thereof, the alignment apertures being oriented to position associated conductive wires approximately perpendicular to a top surface of the substantially planar support member;
a second layer disposed on top of the first layer and comprising a substantially planar chip substrate having at least one imaging array disposed thereon and associated conductive contact points thereon;
a third layer comprising a lens support member disposed at least partially on top of the chip substrate, the lens support member being configured to provide lateral support to a lens system; and
at least one conductive wire disposed within each alignment aperture and positioned to align the first and second layers in a stacked configuration, the conductive wires extending longitudinally along a corresponding side surface of the chip substrate and being operatively coupled to the conductive contact points disposed coplanar with a light surface of the chip substrate.

17. The stacked, miniaturized imaging device of claim 16, further comprising a GRIN lens disposed on a light receiving surface of the chip substrate.

18. The stacked miniaturized imaging device of claim 17, wherein the lens support member extends from a bottom portion of the GRIN lens to at least a middle portion of the GRIN lens.

19. The stacked miniaturized imaging device of claim 16, wherein the first, second, and third layers are not substantially wider than 500 microns.

* * * * *